(12) United States Patent
Koopmans et al.

(10) Patent No.: US 8,957,098 B2
(45) Date of Patent: Feb. 17, 2015

(54) USE OF LEFLUNOMIDE AND MALONONITRILAMIDES

(75) Inventors: Guido Koopmans, JA Sittard (NL); Birgit Hasse, Wuppertal (DE); Stefan Mullner, Langenfeld (DE)

(73) Assignee: ALGIAX Pharmaceuticals GmbH (DE)

(*) Notice: Subject to any disclaimer, the term of this patent is extended or adjusted under 35 U.S.C. 154(b) by 0 days.

(21) Appl. No.: 13/817,800

(22) PCT Filed: Aug. 23, 2011

(86) PCT No.: PCT/EP2011/004218
§ 371 (c)(1),
(2), (4) Date: Feb. 19, 2013

(87) PCT Pub. No.: WO2012/028278
PCT Pub. Date: Mar. 8, 2012

(65) Prior Publication Data
US 2013/0274301 A1 Oct. 17, 2013

Related U.S. Application Data

(60) Provisional application No. 61/376,453, filed on Aug. 24, 2010.

(51) Int. Cl.
*A61K 31/42* (2006.01)
*A61K 31/277* (2006.01)
*A61K 31/167* (2006.01)

(52) U.S. Cl.
CPC ............... *A61K 31/42* (2013.01); *A61K 31/167* (2013.01); *A61K 31/277* (2013.01)
USPC ............................ 514/378; 514/521; 548/248

(58) Field of Classification Search
USPC .................................. 514/378, 521; 548/248
See application file for complete search history.

(56) References Cited

U.S. PATENT DOCUMENTS

| | | | |
|---|---|---|---|
| 3,536,809 A | 10/1970 | Applezweig | |
| 3,598,123 A | 8/1971 | Zaffaroni | |
| 3,845,770 A | 11/1974 | Theeuwes | |
| 3,916,899 A | 11/1975 | Theeuwes | |
| 4,008,719 A | 2/1977 | Theeuwes | |
| 5,059,595 A | 10/1991 | LeGrazie | |
| 5,073,543 A | 12/1991 | Marshall | |
| 5,120,548 A | 6/1992 | McClelland | |
| 5,354,556 A | 10/1994 | Sparks | |
| 5,532,259 A | 7/1996 | Bartlett | |
| 5,556,870 A | 9/1996 | Weithmann | |
| 5,591,767 A | 1/1997 | Mohr | |
| 5,639,476 A | 6/1997 | Oshlack | |
| 5,674,533 A | 10/1997 | Santus | |
| 5,733,566 A | 3/1998 | Lewis | |
| 6,011,051 A * | 1/2000 | Mullner et al. ............... 514/378 |
| 2003/0223960 A1 | 12/2003 | Wettstein | |

FOREIGN PATENT DOCUMENTS

| | | |
|---|---|---|
| EP | 0821952 | 2/1998 |
| EP | 2314291 | 4/2011 |
| WO | 0050079 | 8/2000 |
| WO | 2009133141 | 11/2009 |

OTHER PUBLICATIONS

Neva (Cervical Spine Changes in Rheumatoid Arthritis, Acta University of Tampere, 2001, pp. 1-86).*
Belen, et al., "Leflunomide prevents vasospasm secondary to subarachnoid haemorrhage", ACTA Neurochir., 149(10):1041-8 (2007).
Cohen, et al., "Leflunomide-induced aseptic meningitis", Joint Bone Spine, 71(3):243-5 (2004).
Hines, et al., "Recovert of function following grafting of human bone marrow-derived stromal cells into the injured spinal cord", Neurorehabil Neural Repair, 20:278-96 (2006).
Kuo, et al., "Synthesis, structure-activity relationships, and pharmacokinetic properties of dihydroorotate dehydrogenase inhibitors: 2-cyano-3-cyclopropyl-3-hydroxy-N-[3'-methyl-4'-(trifluoromethyl)phenyl ] propenamide and related compounds", J Med Chem., 39:4608-21 (1996).
Schorlemmer, et al., "Therapeutic activity of malononitrilamides (MNA 279 and MNA 715) an acute and chronic, relapsing, experimental, allergic en ephalomyelitis" ,Drugs Under Exp Clin Res., 23(5-6):175-81 (1997).
Shumsky, et al., "Delayed transplantation of fibroblasts genetically modified to secrete BDNF and NT-3 into a spinal cord injury site is associated with limited recovery of function", Exp. Neural., 184:114-30 (2003).

* cited by examiner

*Primary Examiner* — San-Ming Hui
*Assistant Examiner* — Kathrien Cruz
(74) *Attorney, Agent, or Firm* — Pabst Patent Group LLP

(57) ABSTRACT

The invention relates to the use of polycycloolefins in electronic devices and more specifically to the use of such polycycloolefins as interlayers applied to insulating layers used in electronic devices, the electronic devices that encompass such polycycloolefin interlayers and processes for preparing such polycycloolefin interlayers and electronic devices.

2 Claims, 13 Drawing Sheets

USE OF LEFLUNOMIDE AND MALONONITRILAMIDES

CROSS REFERENCE TO RELATED APPLICATIONS

This application is a 371 application of published International Application No. PCT/EP2011/004218 entitled "Novel Use of Leflunomide and Malononitrilamides", filed in the European Patent Office for the PCT on Aug. 23, 2011, which claims priority to U.S. Ser. No. 61/376,453 filed Aug. 24, 2010 and EP 10008802.0 filed Aug. 24, 2010, all of which are herein incorporated by reference in their entireties.

FIELD OF THE DISCLOSURE

The technology provided herein relates to the novel use of leflunomide and derivatives of the active metabolite thereof in the treatment of central nervous system (CNS)-trauma related disorders.

BACKGROUND

Central nervous system (CNS) trauma, caused by injuries such as spinal and head injuries, cause, when not-fatal, devastating physical and psychological effects to the human body. Many of these injuries are caused by common events such as automobile accidents, serious falls, diving accidents, crushing industrial injuries and gunshot or stab wounds.

Spinal cord injury (SCI) and traumatic brain injury (TBI) cause tissue damage through both direct and indirect, or secondary, means. Direct tissue damage is typically caused by direct mechanical injury to the tissue. Secondary tissue damage is believed to be caused by the activation of endogenous, autodestructive, neurochemical substances. Other types of acute CNS injuries, such as stroke or hypoxia, also exhibit secondary tissue damage that shares many of the secondary injury factors associated with neurotrauma.

Traumatic brain injury (TBI) is an example of mechanical damage. The pathophysiology of TBI can be separated into primary injury and secondary injury. Primary injury occurs at the time of impact, while secondary injury occurs after the impact secondary to the body's response to primary injury. Each of primary and secondary injuries can be subdivided into focal and diffuse types. Focal injury tends to be caused by contact forces, whereas diffuse injury is likely to be caused by noncontact, acceleration-deceleration, or rotational forces.

Diffuse axonal injury (DAI) is caused by forces associated with acceleration-deceleration and rotational injuries. DAI is an axonal shearing injury of the axons that is most often observed in the midline structures, including the parasagittal white matter of the cerebral cortex, the corpus callosum, and the pontine-mesencephalic junction adjacent to the superior cerebral peduncles. Posttraumatic syndrome may develop following traumatic injury. The syndromes include hydrocephalus, altered level of consciousness, headache, migraine, nausea, emesis, memory loss, dizziness, diplopia, blurred vision, emotional lability, sleep disturbances, irritability, inability to concentrate, nervousness, behavioral impairment, cognitive deficit, and epilepsy. Seizures are commonly observed with contusions, depressed skull fracture and severe head injury. Intracranial infections are another potential complication of TBI. When basilar skull fractures or cerebrospinal fluid fistulae are present, the risk of infection is increased. Other causes of CNS injury/damage include neurochemical and cellular changes, hypotension, hypoxia, ischemia, electrolyte imbalances, increased ICP with decreased cerebral perfusion pressure (CPP) and a risk of herniation. Acute loss of circulation to an area of the brain results in ischemia and a corresponding loss of neurologic function. Classified as either hemorrhagic or ischemic, strokes typically manifest with the sudden onset of focal neurologic deficits, such as weakness, sensory deficit, or difficulties with language. Ischemic strokes have a heterogeneous group of causes, including thrombosis, embolism, and hypoperfusion, whereas hemorrhagic strokes can be either intraparenchymal or subarachnoid. As blood flow decreases, neurons cease functioning, and irreversible neuronal ischemia and injury begin at blood flow rates of less than 18 mL/100 mg/min.

The processes involved in stroke injury at the cellular level are referred to as the ischemic cascade. Within seconds to minutes of the loss of glucose and oxygen delivery to neurons, the cellular ischemic cascade begins. The process begins with cessation of the electrophysiologic function of the cells. The resultant neuronal and glial injury produces edema in the ensuing hours to days after stroke, causing further injury to the surrounding neuronal tissues.

Spinal cord injury (SCI) is an insult to the spinal cord resulting in a change, either temporary or permanent, in its normal motor, sensory, or autonomic function.

Primary SCI arises from mechanical disruption, transection, extradural pathology, or distraction of neural elements. This injury usually occurs with fracture and/or dislocation of the spine. However, primary SCI may occur in the absence of spinal fracture or dislocation. Penetrating injuries due to bullets or weapons may also cause primary SCI. More commonly, displaced bone fragments cause penetrating spinal cord or segmental spinal nerve injuries. Extradural pathology may also cause primary SCI. Spinal epidural hematomas or abscesses cause acute cord compression and injury. Spinal cord compression from metastatic disease is a common oncologic emergency. Longitudinal distraction with or without flexion and/or extension of the vertebral column may result in primary SCI without spinal fracture or dislocation.

The pathophysiology of secondary SCI involves a multitude of cellular and molecular events which progress over the first few days after injury. The most important cause of secondary SCI is vascular injury to the spinal cord caused by arterial disruption, arterial thrombosis, and hypoperfusion due to shock. SCI can be sustained through ischemia from damage or impingement on the spinal arteries. SCI due to ischemia can occur during surgery where aortic blood flow is temporarily stopped.

Spinal cord injury can also be caused by toxicity. One of the most compelling toxicity in spinal cord injury is the accumulation and subsequent damage exerted by the excitatory amino acid neurotransmitter. Glutamate induced excitotoxicity causes an elevation of intracellular calcium. Raised intracellular calcium can in turn cause activation of calcium dependent proteases or lipases which cause further damage due to breakdown of cytoskeletal components including neurofilaments and dissolution of cell membranes. The excess production of arachidonic acid and eicosanoids such as prostaglandins may be related to lipid peroxidation and oxygen free radicals. The release of vasoactive eicosanoids from damaged neuronal membranes may in turn cause progressive posttraumatic ischemia by inducing vasospasm. Endogenous opioids may also be involved in the secondary injury process either by their effects on the local or systemic circulation or by direct effects on the injured cord.

Neurogenic shock can result from SCI. Neurogenic shock refers to the hemodynamic triad of hypotension, bradycardia, and peripheral vasodilation resulting from autonomic dysfunction and the interruption of sympathetic nervous system control in acute SCI, and is differentiated from spinal and hypovolemic shock. Hypovolemic shock tends to be associated with tachycardia. Spinal shock is defined as the complete loss of all neurologic function, including reflexes and rectal tone, below a specific level that is associated with autonomic dysfunction. An initial increase in blood pressure is noted due to the release of catecholamines, followed by hypotension. Flaccid paralysis, including of the bowel and bladder, is observed, and sometimes sustained priapism develops. These symptoms tend to last several hours to days until the reflex arcs below the level of the injury begin to function again.

Current therapy for SCI aims to improve motor function and sensation in patients with the disorder. At present, there are no agents that are consistently effective in treating the disorder. Corticosteroids are the mainstay of therapy. Glucocorticoids such as methylprednisolone are thought to reduce the secondary effects of acute SCI, and the use of high-dose methylprednisolone in no penetrating acute SCI has increased over the last decade especially in North America. However, the validities of the results are questionable.

Therefore, new methods and compounds that are able to treat CNS-trauma related disorders are needed.

SUMMARY OF THE DISCLOSURE

In a first aspect, embodiments of this disclosure provide compounds for the use in the treatment of central nervous system (CNS)-trauma related disorders.

In still another aspect, embodiments of this disclosure provide pharmaceutical compositions, single unit dosage forms, and kits suitable for use in the treatment of central nervous system (CNS)-trauma related disorders which comprise compounds according to the present disclosure.

In a further aspect, embodiments of this disclosure relate to methods of treating and preventing CNS-trauma related disorders which comprise administering to a patient in need of such treatment or prevention a therapeutically or prophylactically effective amount of a compound according to this disclosure.

Further, embodiments of this disclosure relate to isoxazole-4-carboxamides or pharmaceutically acceptable salts, solvates, hydrates, stereoisomers, clathrates, or prodrugs thereof for use in the treatment of central nervous system (CNS)-trauma related disorders.

In other aspects, this disclosure relates to malononitrilamides or pharmaceutically acceptable salts, solvates, hydrates, stereoisomers, clathrates, or prodrugs thereof for use in the treatment of central nervous system (CNS)-trauma related disorders.

Further, embodiments of this disclosure relate to the use of leflunomide or malononitrilamides for use in the treatment of central nervous system (CNS)-trauma related disorders.

DETAILED DESCRIPTION OF THIS DISCLOSURE

Figure 1:
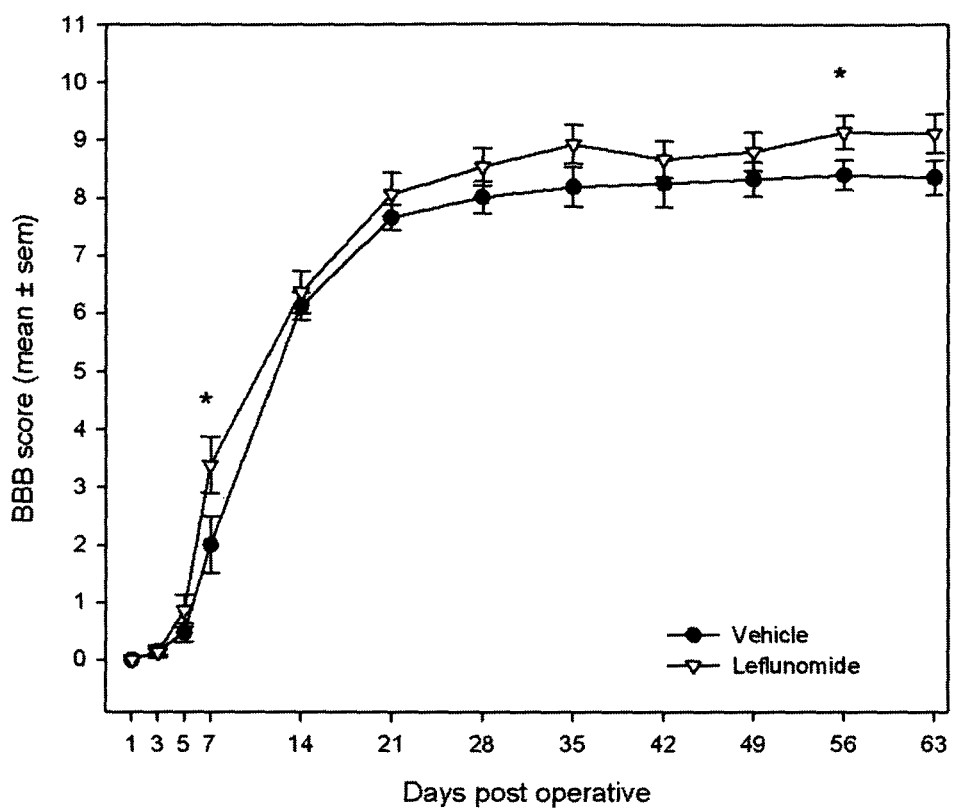
FIG. 1. shows the BBB score after contusion and oral gavage of leflunomide

Disclosed herein are the use of leflunomide, active metabolites and/or derivatives thereof for the treatment of central nervous system (CNS)-trauma related disorders.

For example, (CNS)-trauma related disorders include complete spinal cord injury, incomplete spinal cord injury, spinal cord contusion, spinal cord compression, spinal cord trauma, spinal injury, paraplegia, quadriplegia, tetraplegia, central cord syndrome, Brown-Séquard syndrome, anterior cord syndrome, conus medullaris syndrome, cauda equina syndrome, traumatic brain injury, TBI, brain injury, brain damage, head injury, diffuse axonal injury (DAI), head trauma, brain concussion, brain contusion, subdural hematoma, epidural hematoma, subarachnoid hemorrhage, intracerebral hemorrhage, and CNS compression.

In advantageous embodiments of the present invention, the (CNS)-trauma related disorder is a spinal cord injury like complete spinal cord injury, incomplete spinal cord injury, spinal cord contusion, spinal cord compression, spinal cord trauma, spinal injury. In advantageous embodiments the (CNS)-trauma related disorder is spinal cord contusion.

In further advantageous embodiments, the compound used in the treatment of trauma related disorders is leflunomide, active metabolites of leflunomide and/or malononitrilamides.

In an advantageous embodiment the active metabolite of leflunomide is a malononitrilamide and/or a derivative thereof.

Leflunomide and its main metabolite, malononitrilamide (MNA), were first made by Hoechst Marion Roussel.

For example the malononitrilamide 715 (FK778) is derived from the active metabolite of leflunomide Teriflunomide (previously A77 1726).

Specific compounds of the disclosure are such derivatives and metabolites described in U.S. Pat. No. 5,532,259, in the international patent application WO 91/717748 and in Kuo et al., (Kuo et al., 1996), each of which is incorporated herein by reference.

In some embodiments also leflunomide analogs described in WO 2004/006834 A2 are used for the treatment as described in the present disclosure.

In Kuo et al., (Kuo et al., 1996) examples for the preparation of compounds according to the present description is shown, each of which is incorporated herein by reference.

In advantageous embodiments, the derivatives of the active metabolite of leflunomide are malononitrilamides or pharmaceutically acceptable salts, solvates or stereoisomers thereof.

Specific examples of compounds used for the treatment of (CNS)-trauma related disorders include, but not limited to compounds with the following structures (formula I to VI):

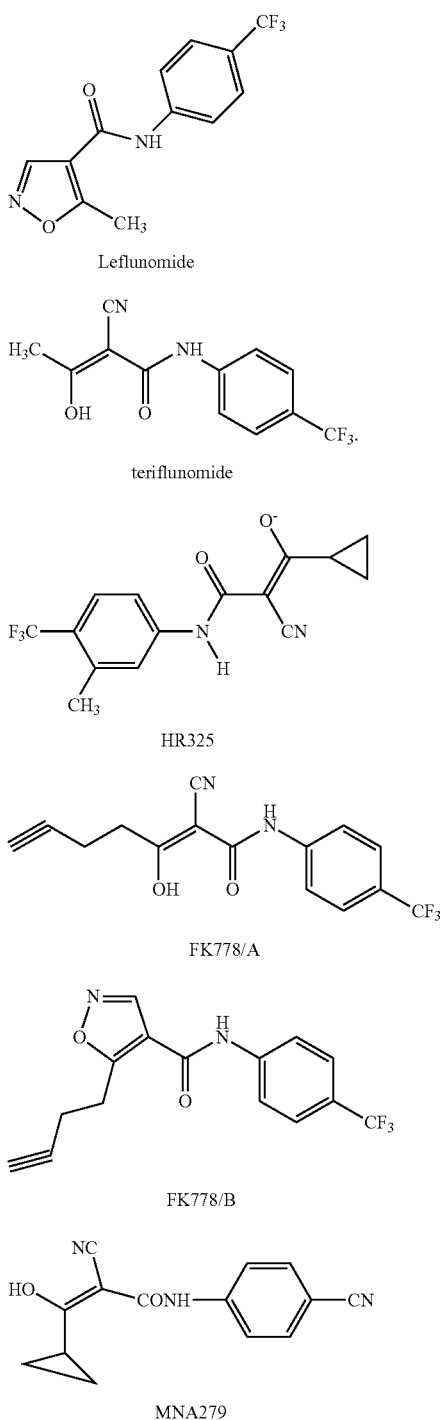

In further advantageous embodiments, the compound is N-(4-trifluoromethylphenyl)-5-methylisoxazol-4-carboxamide, N-(4-trifluoromethyl)-phenyl-2-cyano-3-hydroxy-crotonic acidamide, 1(3-methyl-4-trifluoro methylphenyl-carbamoyl)-2-cyclopropyl-2oxo-propionitrile, is N-(4-trifluoromethyl)-phenyl-2-cyano-3-hydroxy-hept-2-en-6-in-carboxylic acidamide and 2-cyano-3-cyclopropyl-3-oxo-(4-cyanophenyl)propionamide or a pharmaceutically acceptable salt, solvate or stereoisomer thereof.

In advantageous embodiments, the compound is 1(3-methyl-4-trifluoro methylphenyl-carbamoyl)-2-cyclopropyl-2oxo-propionitrile or N-(4-trifluoromethyl)-phenyl-2-cyano-3-hydroxy-crotonic acidamide.

In further advantageous embodiments, the compound has the structure with the formula I or III.

In further advantageous embodiments, a compound according to the present invention is used as the only physically active compound in the treatment of CNS-trauma related disorders without a second active agent.

In yet other advantageous embodiments, the disclosure relates to pharmaceutical compositions for preventing and/or treating CNS-trauma related disorders, which comprises a therapeutically effective amount of a compound according to the present disclosure in admixture with a pharmaceutical acceptable carrier or excipient.

In advantageous embodiments, the pharmaceutical composition according to the present invention comprises a compound according to the present invention and no second active ingredient in the composition. In an advanced embodiment, leflunomide is used as the sole active agent for the treatment of CNS-trauma related disorders. In an advanced embodiment, leflunomide is used for the treatment of CNS-trauma related disorders without an immunomodulatory compound as a second active agent.

In advantageous embodiments, the pharmaceutical composition is used for preventing and/or treating CNS-trauma related disorders, whereby the composition comprises a therapeutically effective amount of leflunomide or a physiologically functional derivative thereof in admixture with a pharmaceutical acceptable carrier or excipient. In advantageous embodiments the pharmaceutical composition comprises a malononitrilamide selected from the group consisting of N-(4-trifluoromethyl)-phenyl-2-cyano-3-hydroxy-crotonic acidamide, (1(3-methyl-4-trifluoro methylphenyl-carbamoyl)-2-cyclopropyl-2oxo-propionitrile), N-(4-trifluoromethyl)-phenyl-2-cyano-3-hydroxy-hept-2-en-6-in-carboxylic acidamide, and 2-cyano-3-cyclopropyl-3-oxo-(4-cyanophenyl)propionamide or a pharmaceutically acceptable salt, solvate or stereoisomer thereof.

Compounds according to the invention can either be commercially purchased or prepared according to the methods described in the publications, patents or patent publications disclosed herein. Further, optically pure compositions can be asymmetrically synthesized or resolved using known resolving agents or chiral columns as well as other standard synthetic organic chemistry techniques. Compounds used in the disclosure may include compounds that are racemic, stereomerically enriched or stereomerically pure, and pharmaceutically acceptable salts, solvates, stereoisomers, and prodrugs thereof.

Preferred compounds used according to the invention are small organic molecules having a molecular weight less than about 1,000 g/mol, and are not proteins, peptides, oligonucleotides, oligosaccharides or other macromolecules.

As used herein and unless otherwise indicated, the term "pharmaceutically acceptable salt" encompasses non-toxic acid and base addition salts of the compound to which the term refers. Acceptable non-toxic acid addition salts include those derived from organic and inorganic acids or bases know in the art, which include, for example, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embolic acid, enanthic acid, and the like. Compounds that are acidic in nature are capable of forming salts with various pharmaceutically acceptable bases. The bases that can be used to prepare pharmaceutically acceptable base addition salts of such acidic compounds are those that form non-toxic base addition salts, i.e., salts containing pharmacologically acceptable cations such as, but not limited to, alkali metal or alkaline earth metal salts and the calcium, magnesium, sodium or potassium salts in particular. Suitable organic bases include, but are not limited to, N,N-dibenzylethylenediamine, chloroprocaine, choline, diethanolamine, ethylenediamine, meglumaine (N-methylglucamine), lysine, and procaine.

As used herein, and unless otherwise specified, the term "solvate" means a compound of the present disclosure or a salt thereof that further includes a stoichiometric or non-stoichiometric amount of solvent bound by non-covalent intermolecular forces. Where the solvent is water, the solvate is a hydrate.

As used herein and unless otherwise indicated, the term "prodrug" means a derivative of a compound that can hydrolyze, oxidize, or otherwise react under biological conditions (in vitro or in vivo) to provide the compound. Examples of prodrugs include, but are not limited to, derivatives of compounds according to the present disclosure that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of immunomodulatory compounds of the disclosure that comprise —NO, —NO2, —ONO, or —ONO2 moieties. Prodrugs can typically be prepared using well-known methods, such as those described in Burger's Medicinal Chemistry and Drug Discovery, 172-178, 949-982 (Manfred E. Wolff ed., 5th ed. 1995), and Design of Prodrugs (H. Bundgaard ed., Elselvier, N.Y. 1985). As used herein and unless otherwise indicated, the terms "biohydrolyzable amide," "biohydrolyzable ester," "biohydrolyzable carbamate," "biohydrolyzable carbonate," "biohydrolyzable ureide," "biohydrolyzable phosphate" mean an amide, ester, carbamate, carbonate, ureide, or phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, lower acyloxyalkyl esters (such as acetoxymethyl, acetoxyethyl, aminocarbonyloxymethyl, pivaloyloxymethyl, and pivaloyloxyethyl esters), lactonyl esters (such as phthalidyl and thiophthalidyl esters), lower alkoxyacyloxyalkyl esters (such as methoxycarbonyl-oxymethyl, ethoxycarbonyloxyethyl and isopropoxycarbonyloxyethyl esters), alkoxyalkyl esters, choline esters, and acylamino alkyl esters (such as acetamidomethyl esters). Examples of biohydrolyzable amides include, but are not limited to, lower alkyl amides, [alpha]-amino acid amides, alkoxyacyl amides, and alkylaminoalkylcarbonyl amides. Examples of biohydrolyzable carbamates include, but are not limited to, lower alkylamines, substituted ethylenediamines, amino acids, hydroxyalkylamines, heterocyclic and heteroaromatic amines, and polyether amines.

As used herein, and unless otherwise specified, the term "stereoisomer" encompasses all enantiomerically/stereomerically pure and enantiomerically/stereomerically enriched compounds of this disclosure. Furthermore, the term "stereoisomer" includes also tautomers which are isomers of organic compounds that readily interconvert by a chemical reaction (tautomerization).

As used herein, and unless otherwise indicated, the term "stereomerically pure" or "enantiomerically pure" means that a compound comprises one stereoisomer and is substantially free of its counter stereoisomer or enantiomer. For example, a compound is stereomerically or enantiomerically pure when the compound contains 80%, 90%, or 95% or more of one stereoisomer and 20%, 10%, or 5% or less of the counter stereoisomer, in certain cases, a compound of the disclosure is considered optically active or stereomerically/enantiomerically pure {i.e., substantially the R-form or substantially the S-form) with respect to a chiral center when the compound is about 80% ee (enantiomeric excess) or greater, preferably, equal to or greater than 90% ee with respect to a particular chiral center, and more preferably 95% ee with respect to a particular chiral center.

As used herein, and unless otherwise indicated, the term "stereomerically enriched" or "enantiomerically enriched" encompasses racemic mixtures as well as other mixtures of stereoisomers of compounds of this disclosure {e.g., R/S=30/70, 35/65, 40/60, 45/55, 55/45, 60/40, 65/35 and 70/30). Various inhibitor compounds of the present disclosure contain one or more chiral centers, and can exist as racemic mixtures of enantiomers or mixtures of diastereomers. This disclosure encompasses the use of stereomerically pure forms of such compounds, as well as the use of mixtures of those forms. For example, mixtures comprising equal or unequal amounts of the enantiomers of a particular inhibitor compound of the disclosure may be used in methods and compositions of the disclosure. These isomers may be asymmetrically synthesized or resolved using standard techniques such as chiral columns or chiral resolving agents. See, e.g., Jacques, J., et al, Enantiomers, Racemates and Resolutions (Wiley-Interscience, New York, 1981); Wilen, S. H., et al, Tetrahedron 33:2725 (1977); Eliel, E. L., Stereochemistry of Carbon Compounds (McGraw-Hill, NY, 1962); and Wilen, S. H., Tables of Resolving Agents and Optical Resolutions p. 268 (E. L. Eliel, Ed., Univ. of Notre Dame Press, Notre Dame, Ind., 1972).

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

The term "physiologically functional derivative" as used herein refers to compounds which are not pharmaceutically active themselves but which are transformed into their pharmaceutical active form in vivo, i.e. in the subject to which the compound is administered. Examples of physiologically functional derivatives are prodrugs such as those described below in the present application.

The term "derivative" as used herein refers to a compound that is derived from a similar compound or a compound that can be imagined to arise from another compound, if one atom is replaced with another atom or group of atoms. The term "derivative" as used herein refers also to a compound that at least theoretically can be formed from the precursor compound (see Oxford Dictionary of Biochemistry and Molecular Biology. Oxford University Press. ISBN 0-19-850673-2.) In advantageous embodiments of the present disclosure the term "derivative" is used for derivatives from leflunomide and/or from active metabolites of leflunomide like teriflunomide. Advantageous embodiments of derivatives of teriflunomide are malononitrilamides and/or derivatives thereof.

The disclosure is also directed to the use of compounds of the formula I, II, III, IV, V or of formula VI and of their pharmacologically tolerable salts or physiologically functional derivatives for the production of a medicament for the prevention and treatment of CNS-trauma.

Methods and uses according to the present disclosure encompass methods of preventing, treating and/or managing CNS injury/damage and related syndromes and CNS-trauma related disorders and CNS-trauma related conditions including, but are not limited to, primary brain injury, secondary brain injury, traumatic brain injury, focal brain injury, diffuse axonal injury, head injury, concussion, post-concussion syndrome, cerebral contusion and laceration, subdural hematoma, epidermal hematoma, posttraumatic epilepsy, chronic vegetative state, complete SCI, incomplete SCI, acute SCI, subacute SCI, chronic SCI, central cord syndrome, Brown-Sequard syndrome, anterior cord syndrome, conus medullaris syndrome, cauda equina syndrome, neurogenic shock, spinal shock, altered level of consciousness, headache, nausea, emesis, memory loss, dizziness, diplopia, blurred vision, emotional lability, sleep disturbances, irritability, inability to concentrate, nervousness, behavioral impairment, cognitive deficit, and seizure.

The symptoms, conditions and/or disorders associated with CNS injury/damage and CNS-trauma include, but are not limited to, motor weakness (especially paraparesis or quadriparesis with or without respiratory distress); loss of sensation or bowel or bladder control; sexual dysfunction; symptoms of neurogenic shock such as lightheadedness, diaphoresis, bradycardia, hypothermia, hypotension without compensatory tachycardia; respiratory insufficiency; quadriplegia with upper and lower extremity areflexia; anesthesia below the affected level; loss of rectal and bladder sphincter tone; urinary and bowel retention leading to abdominal distention, ileus, and delayed gastric emptying; ipsilateral ptosis, miosis, anhydrosis; paralysis with loss of temperature sensation; relative sparing of touch, vibration, and proprioception; dissociated sensory loss; arm weakness, patch sensory loss below the level of the lesion; loss of vibration and position sense below the level of the lesion, hyperreflexia, and an extensor toe sign; ipsilateral segmental anesthesia; and polyradiculopathy, radicular sensory changes, asymmetric lower motor neuron-type leg weakness, and sphincter disturbances.

The suitability of a particular route of administration of an compound according to the present disclosure employed for a particular active agent will depend on the active agent itself (e.g., whether it can be administered orally without decomposing prior to entering the blood stream) and the disease being treated. An advantageous embodiment of the route of administration for a compound according to the present disclosure is orally. Further routes of administration are known to those of ordinary skill in the art.

The dosage of therapeutically effective amount of at least one compound varies from and also depends upon the age and condition of each individual patient to be treated. In an embodiment of the present disclosure, the recommended daily dose range of a compound according to the present disclosure for the conditions and disorders described herein lies within the range of from about, a daily dose of about 1 mg-10 g/body, preferable 5 mg-5 g/body and more preferable 10 mg-2 g/body of the active ingredient is generally given for preventing and/or treating this disease, and an average single dose of about 0.5-1 mg, 5 mg, 10 mg, 50 mg, 100 mg, 250 mg, 500 mg, 1 g, 2 g and 3 g is generally administered. Daily dose for administration in humans for preventing this disease (CNS trauma related disorders) could be in the range of about 0.1-50 mg/kg.

In a preferred embodiment the recommended daily dose range of at least one compound according to the present disclosure for the conditions and disorders described herein lies within the range of from about 3 to 50 mg/kg/day, preferably within the range of from about 5 to 40 mg/kg/day, more preferably within the range of from about 7 to 30 mg/kg/day. In a preferred embodiment the daily dose range of at least one compound according to the present disclosure for the conditions and disorders described herein is within the range of 7 and 14 mg/kg/day, preferably in human.

While the term for administering of at least one compound to prevent this disease (CNS trauma related disorders) varies depending on species, and the nature and severity of the condition to be prevented, the compound may usually be administered to humans for a short term or a long term, i.e. for 1 week to 1 year.

Pharmaceutical compositions can be used in the preparation of individual, single unit dosage forms. The compounds of the present disclosure can be used in the form of pharmaceuticals compositions, for example, in solid, semisolid or liquid form, which contains one or more of the compounds according to the present disclosure as active ingredient associated with pharmaceutically acceptable carriers or excipient suitable for oral, parenteral such as intravenous, intramuscular, intrathecal, subcutaneous, enteral, intrarectal or intranasal administration. The active ingredient may be compounded, for example, with the usual non-toxic, pharmaceutically acceptable carriers for tablets, pellets, capsules, suppositories, solutions (saline for example), emulsion, suspensions (olive oil, for example), ointment and any other form suitable for use. The carriers which can be used are water, glucose, lactose gum acacia, gelatine, manitol, starch paste, magnesium trisilicate, corn starch, keratin, colloidal silica, potato starch, urea and other carriers suitable for use in manufacturing preparations, in solid, semisolid or liquid form, and in addition auxiliary, stabilizing, thickening and colouring agents and perfumes may be used. The active object compound is included in the pharmaceutical composition in an effective amount sufficient to prevent and/or treat the disease.

Single unit dosage forms of the disclosure are suitable for oral, mucosal (e.g., nasal, sublingual, vaginal, buccal, or rectal), parenteral (e.g., subcutaneous, intravenous, bolus injection, intramuscular, or intraarterial), topical (e.g., eye drops or other ophthalmic preparations), transdermal or transcutaneous administration to a patient. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient.

The composition, shape, and type of dosage forms of the disclosure will typically vary depending on their use. For example, a dosage form used in the acute treatment of a disease may contain larger amounts of one or more of the active agents it comprises than a dosage form used in the chronic treatment of the same disease. Similarly, a parenteral dosage form may contain smaller amounts of one or more of the active agents it comprises than an oral dosage form used to treat the same disease. These and other ways in which specific dosage forms encompassed by this disclosure will vary from one another will be readily apparent to those skilled in the art. See, e.g., Remington's Pharmaceutical Sciences, 18th ed., Mack Publishing, Easton Pa. (1990).

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active agents in the dosage form. For example, the decomposition of some active agents may be accelerated by some excipients such as lactose, or when exposed to water. Active agents that comprise primary or secondary amines are particularly susceptible to such accelerated decomposition. Consequently, this disclosure encompasses pharmaceutical compositions and dosage forms that contain little, if any, lactose or other mono- or di-saccharides. As used herein, the term "lactose-free" means that the amount of lactose present, if any, is insufficient to substantially increase the degradation rate of an active ingredient.

Lactose-free compositions of the disclosure can comprise excipients that are well known in the art and are listed, for example, in the U.S. Pharmacopeia (USP) 25-NF20 (2002). In general, lactose-free compositions comprise active ingredients, a binder/filler, and a lubricant in pharmaceutically compatible and pharmaceutically acceptable amounts. Preferred lactose-free dosage forms comprise active ingredients, microcrystalline cellulose, pre-gelatinized starch, and magnesium stearate.

This disclosure further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, Drug Stability: Principles & Practice, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the disclosure can be prepared using anhydrous or low moisture containing ingredients and low moisture or low humidity conditions. Pharmaceutical compositions and dosage forms that comprise lactose and at least one active ingredient that comprise a primary or secondary amine are preferably anhydrous if substantial contact with moisture and/or humidity during manufacturing, packaging, and/or storage is expected. An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g. vials), blister packs, and strip packs.

The disclosure further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active agents in a dosage form may differ depending on factors such as, but not limited to, the route by which it is to be administered to patients. However, typical dosage forms of the disclosure comprise a compound according to the present disclosure or a pharmaceutically acceptable salt, solvate, hydrate, stereoisomer, clathrate, or prodrug thereof in an amount of from about 0.10 to about 150 mg. Typical dosage forms comprise a compound according to the present disclosure or a pharmaceutically acceptable salt, solvate, hydrate, stereoisomer, clathrate, or prodrug thereof in an amount of about 0.1, 1, 2, 5, 7.5, 10, 12.5, 15, 17.5, 20, 25, 50, 100, 150 or 200 mg. In a particular embodiment, a preferred dosage form comprises a compound according to the present description in an amount of about 1, 2, 5, 10, 25 or 50 mg. In a specific embodiment, a preferred dosage form comprises a compound according to the present description in an amount of about 5, 10, 25 or 50 mg.

Oral Dosage Forms of pharmaceutical compositions of the disclosure that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences, 18th ed., Mack Publishing, Easton Pa. (1990).

Typical oral dosage forms of the disclosure are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms {e.g., powders, tablets, capsules, and caplets) include, but are not limited to, starches, sugars, microcrystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the disclosure include, but are not limited to, binders, fillers, disintegrants, and lubricants. Binders suitable for use in pharmaceutical compositions and dosage forms include, but are not limited to, corn starch, potato starch, or other starches, gelatine, natural and synthetic gums such as acacia, sodium alginate, alginic acid, other alginates, powdered tragacanth, guar gum, cellulose and its derivatives {e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, {e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM. Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the disclosure is typically present in from about 50 to about 99 weight percent of the pharmaceutical composition or dosage form.

Disintegrants are used in the compositions of the disclosure to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the disclosure. The amount of disintegrant used varies based upon the type of formulation, and is readily discernible to those of ordinary skill in the art. Typical pharmaceutical compositions comprise from about 0.5 to about 15 weight percent of disintegrant, preferably from about 1 to about 5 weight percent of disintegrant.

Disintegrants that can be used in pharmaceutical compositions and dosage forms of the disclosure include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms of the disclosure include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL200, manufactured by W.R. Grace Co. of Baltimore, Md.), a coagulated aerosol of synthetic silica (marketed by Degussa Co. of Piano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

A preferred solid oral dosage form of the disclosure comprises a compound of the disclosure, anhydrous lactose, microcrystalline cellulose, polyvinylpyrrolidone, stearic acid, colloidal anhydrous silica, and gelatin.

Active ingredients of the disclosure can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein can be readily selected for use with the active ingredients of the disclosure. The disclosure thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

Parenteral dosage forms can be administered to patients by various routes including, but not limited to, subcutaneous, intravenous (including bolus injection), intramuscular, and intra-arterial. Because their administration typically bypasses patients' natural defences against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. Suitable vehicles that can be used to provide parenteral dosage forms of the disclosure are well known to those skilled in the art.

Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the disclosure. For example, cyclodextrin and its derivatives can be used to increase the solubility of a compound of the disclosure and its derivatives. See, e.g., U.S. Pat. No. 5,134,127, which is incorporated herein by reference.

Topical and mucosal dosage forms of the disclosure include, but are not limited to, sprays, aerosols, solutions, emulsions, suspensions, eye drops or other ophthalmic preparations, or other forms known to one of skill in the art. See, e.g., Remington's Pharmaceutical Sciences, 16th and 18th eds., Mack Publishing, Easton Pa. (1980 & 1990); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels.

Suitable excipients {e.g., carriers and diluents) and other materials that can be used to provide topical and mucosal dosage forms encompassed by this disclosure are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are non-toxic and pharmaceutically acceptable. Moisturizers or humectants can also be added to pharmaceutical compositions and dosage forms if desired. Examples of such additional ingredients are well known in the art. See, e.g., Remington's Pharmaceutical Sciences, 16th and 18th eds., Mack Publishing, Easton Pa. (1980 & 1990).

The pH of a pharmaceutical composition or dosage form may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

Typically, active ingredients of the disclosure are preferably not administered to a patient at the same time or by the same route of administration. This disclosure therefore encompasses kits which, when used by the medical practitioner, can simplify the administration of appropriate amounts of active ingredients to a patient.

A typical kit of the disclosure comprises a dosage form of an compound of the disclosure, or a pharmaceutically acceptable salt, solvate, hydrate, stereoisomer, prodrug, or clathrate thereof. Kits encompassed by this disclosure can further comprise additional active agents. Examples of the additional active agents include, but are not limited to, those disclosed herein (see, e.g., section 4.2). Kits of the disclosure can further comprise devices that are used to administer the active ingredients. Examples of such devices include, but are not limited to, syringes, drip bags, patches, and inhalers. In an advantageous embodiment, a kit of the disclosure contains leflunomide and no additional immunomodulatory compound.

Kits of the disclosure can further comprise cells or blood for transplantation as well as pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Advantageous examples for compounds according to the present disclosure for the use in the treatment of CNS-trauma related disorders are:
A) Leflunomide (N-(4-trifluoromethylphenyl)-5-methyl-isoxazol-4-carboxamide)
B) A77-1726 (teriflunomide) (N-(4-trifluoromethyl)-phenyl-2-cyano-3-hydroxy-crotonic acidamide)
C) HR325 (Laflunimus) (1(3-methyl-4-trifluoro methylphenyl-carbamoyl)-2-cyclopropyl-2oxo-propionitrile)
D) FK778 (N-(4-trifluoromethyl)-phenyl-2-cyano-3-hydroxy-hept-2-en-6-in-carboxylic acidamide)
E) MNA279 (2-cyano-3-cyclopropyl-3-oxo-(4-cyanophenyl)propionamide)

The following examples and methods are offered for illustrative purposes only, and are not intended to limit the scope of the present disclosure in any way.

METHODS AND EXAMPLES

A series of non-clinical pharmacology and toxicology studies have been performed to support the clinical evaluation of the compounds according to the present disclosure in human subjects. These studies were performed in accordance with internationally recognized guidelines for study design and in compliance with the requirements of Good Laboratory Practice (GLP) unless otherwise noted.

Example 1

Leflunomide treatment to improve locomotor recovery after severe spinal cord contusion injury in the rat.

Surgical Methods

Thirteen week-old female Lewis rats (Charles River, Sulzfeld Germany) were housed under a 12:12 h dark/light regime and allowed free access to water and food. After one week of habituation the animals underwent general anesthesia with a mixture of isoflurane and air (induction: 5% isoflurane, maintenance: 2.2% isofluorane). A Th10 laminectomy was performed without rupturing the dura and a severe contusive SCI (25 gem NYU/MASCIS II impactor) {Gruner, 1992 #3} was induced. After suturing muscle and skin, a subcutaneous (s.c.) injection of 5 ml of Ringers Lactate was given. Bladders were emptied manually 2 times a day until spontaneous voiding returned (usually within 1 week). The lesion severity was verified by the impact velocity and contusion depth of the impactor rod. Animals with an impact velocity error >5% were excluded from further analysis. After injury, individual rats were randomly assigned into a treatment group. The following groups were used:

Group 1: SCI+vehicle (1.5% CMC in sterile water) by gavage for 7 days

Group 2: SCI+LEF (20 mg/kg/day) in vehicle by gavage for 7 days

The BBB Open Field Locomotor Rating Scale:

The BBB locomotor rating scale is an "open field locomotion score" developed to assess functional recovery after spinal cord injury in rats (Basso et al., 1995). The BBB score is scaled from 0 to 21 points, a BBB score of 0 represents a complete paralysis of the hind limbs and a BBB score of 21 represents normal locomotion. In between 0 and 21 points there are several "milestones" of functional recovery, the most important milestone after a severe contusion injury is a BBB score >9. A BBB score >9 means the animal has reached the level of "weight supported plantar stepping" or "walking". Animals with a BBB score of <9 are not able to walk.

The BBB locomotor rating scale was used according to the present disclosure to assess general locomotor performance. The score was assessed before injury and at 1, 3, 5, 7, 14, 21, 35, 42, 49, 56 and 63 days post operation (dpo) by 2 blinded observers.

Explorative Rearing Test:

When placed in a Plexiglas cylinder (18 cm diameter×35.0 cm height), animals spontaneously rear and contact the walls with their forepaws. Numbers, duration and types of rears were analyzed during the 3-min recorded observation period in the cylinder (Himes et al., 2006; Shumsky et al., 2003). A mirror was placed at an angle behind the cylinder so that the forelimbs could be viewed at all times. The testing session was videotaped, and rearing behaviour was scored blindly at a later date.

Different types of rears of increasing heights were observed:

LEVEL 1: Crouch—Animals lifted both forepaws off the ground up to 10 cm;

LEVEL 2: Rear—Animals reared and extended the trunk with the hindlimbs flexed reaching a height between 10 and 15 cm;

LEVEL 3: Stand—Animals reared and extended the trunk with the hindlimbs extended reaching a height over 15 cm.

Occasionally an animal progressed through several types of rears before touching down, in which case the time the animal spend in each rearing height was measured by counting the single video frames. In the Explorative rearing test, the shown parameter presents the average time each animal spends at the different rearing levels. Most animals don't have any problem with exploring the LEVEL 1 rearing height, because they all spend a similar amount of time at this LEVEL. Physically more demanding is the LEVEL 2 rearing height between 10 to 15 cm, here most of the treatment effects were observed. Treated animals tend to spend more exploration time at this level when compared to vehicle controls. This cannot be explained by a lack of exploration or curiosity because there is no difference in the number of rearing attempts between treated animals and vehicle controls. The biggest challenge is to explore LEVEL 3 which is >15 cm. At this LEVEL the functional impairment as a consequence of the SCI becomes most obvious. With or without treatment the animals are barely able to explore this LEVEL, whereas for the healthy control animals this is not a problem.

Results:

Functional Recovery

The functional recovery as assessed by the BBB locomotor rating scale followed a pattern of progressive recovery over the first 2-3 weeks after injury. Thereafter the spontaneous functional recovery reached a 'steady state'. Significant effects of the Leflunomide treatment were noted at DPO 7 and DPO 56. FIG. 1 shows the functional recovery as assessed by the BBB locomotor rating scale. (*p<0.05)

Figure 2:
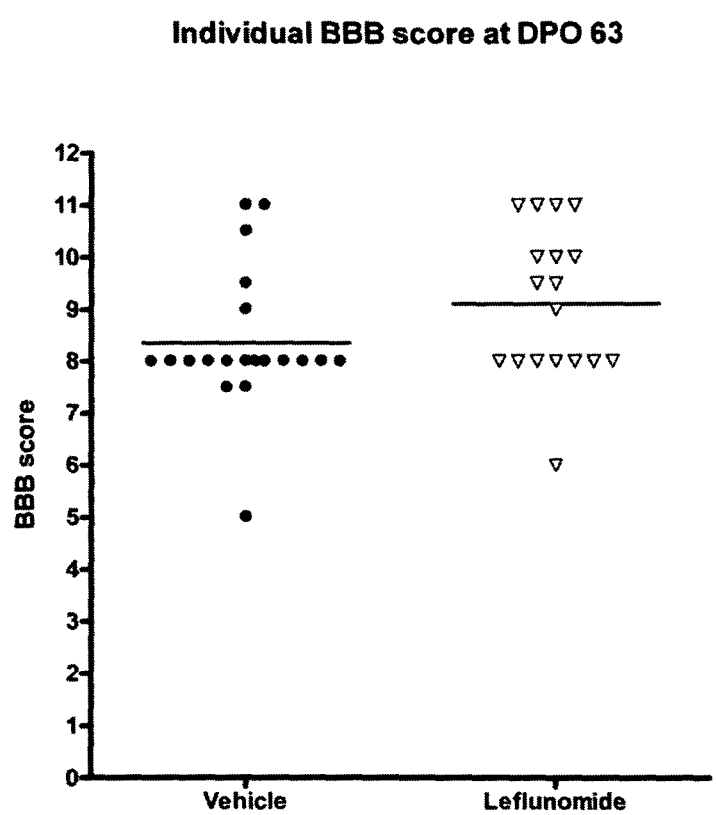
FIG. 2. shows the individual BBB score at DPO63 of the leflunomide treated and vehicle control animals FIG. 3. shows the results of the explorative rearing test in vehicle control animals, leflunomide treated animals and healthy control animals FIG. 4. shows the BBB score after contusion and oral gavage of 20 mg HR325 treatment FIG. 5. shows the individual BBB score at DPO63 of the 20 mg HR325 treated animals and vehicle control animals FIG. 6. shows the results of the explorative rearing test in vehicle control animals, 20 mg HR325 treated animals and healthy control animals FIG. 7. shows the BBB score after contusion and oral gavage of 3 mg, 20 mg and 60 mg HR325 treatment FIG. 8. shows the individual BBB score at DPO63 of the 3 mg, 20 mg and 60 mg HR325 treated animals and vehicle control animals FIG. 9. shows the results of the explorative rearing test in vehicle control animals, 3 mg and 20 mg HR325 treated animals and healthy control animals FIG. 10. shows the BBB score after contusion and oral gavage of 3 mg and 10 mg teriflunomide treatment FIG. 11. shows the individual BBB score at DPO63 of the 3 mg and 10 mg teriflunomide treated animals and vehicle control animals FIG. 12. shows the BBB score after contusion and oral gavage of 10 mg, and 30 mg HR325 treatment FIG. 13. shows the individual BBB score at DPO63 of the 10 mg and 30 mg HR325 treated animals and vehicle control animals

At the end of the experiment the Leflunomide treated animals performed better as compared to the vehicle controls. (Mann-Whitney U Test; p=0.062, see FIG. 2). FIG. 2 shows individual BBB scores of the Leflunomide and Vehicle treated animals at DPO 63.

The explorative rearing test was used to assess other aspects of functional recovery after injury. One of the parameters that reflect the degree of functional recovery in this test is the time each animal spend in the different rearing heights. The results of this parameter are presented in FIG. 3.

Figure 3:
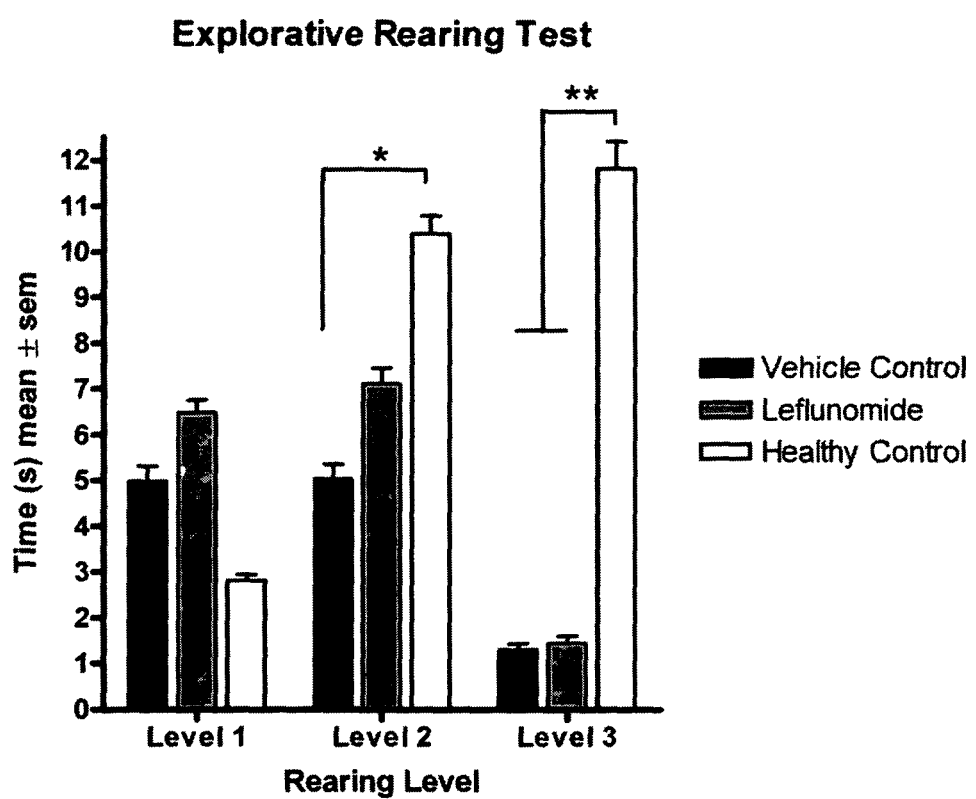

These results clearly demonstrate that the rearing attempts of leflunomide treated animals are longer in time and that the forepaws reached higher levels when compared to vehicle control animals. This effect was most obvious in LEVEL 2 (10-15 cm); vehicle control animals spend significantly less time in LEVEL 2 when compared to healthy control animals, whereas this is not the case for leflunomide treated animals (see FIG. 3). At LEVEL 3 (>15 cm) the impairment as a consequence of the spinal cord contusion becomes obvious, the healthy control animals spend most of their exploring time in the highest level, significantly longer as both leflunomide treated animals and vehicle controls. FIG. 3 shows the results of the explorative rearing test in vehicle controls and leflunomide treated animals (*p<0.05, **p<0.01).

Altogether, the data presented in example 1 showed that leflunomide treatment improves functional recovery after severe spinal cord contusion in the rat.

Example 2

HR325 (Laflunimus) treatment can improve locomotor recovery after severe spinal cord contusion injury in the rat.

For surgical methods see example 1.

After injury, individual rats were randomly assigned into a treatment group. The following groups were used:

Group 1: SCI+vehicle (1.5% CMC in sterile water) by gavage for 7 days

Group 2: SCI+HR325 (20 mg/kg/day) in vehicle by gavage for 7 days

For the BBB open field locomotor rating scale see example 1.

For the explorative rearing test see example 1.

Results:

Functional Recovery

Figure 4:
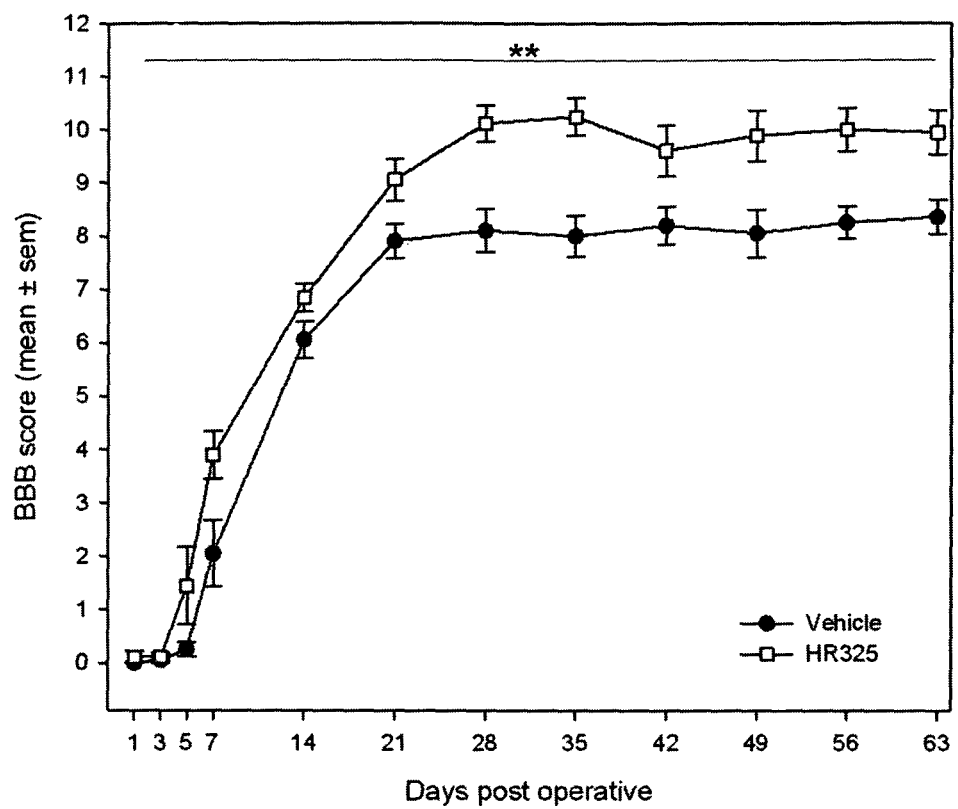

The functional recovery as assessed by the BBB locomotor rating scale followed a pattern of progressive recovery over the first 2-3 weeks after injury. Thereafter the spontaneous functional recovery reached a 'steady state'. However the HR325 treated animals reached a steady state at a BBB score of around 10, whereas the vehicle treated animals reached a BBB score of 8.3. This effect was distinct from DPO 7 up till the end at DPO 63 (ANOVA-RM; Treatment $F_{1,27}=11.3$ p=0.002). FIG. 4 shows the functional recovery as assessed by the BBB locomotor rating scale (**p<0.01).

Figure 5:
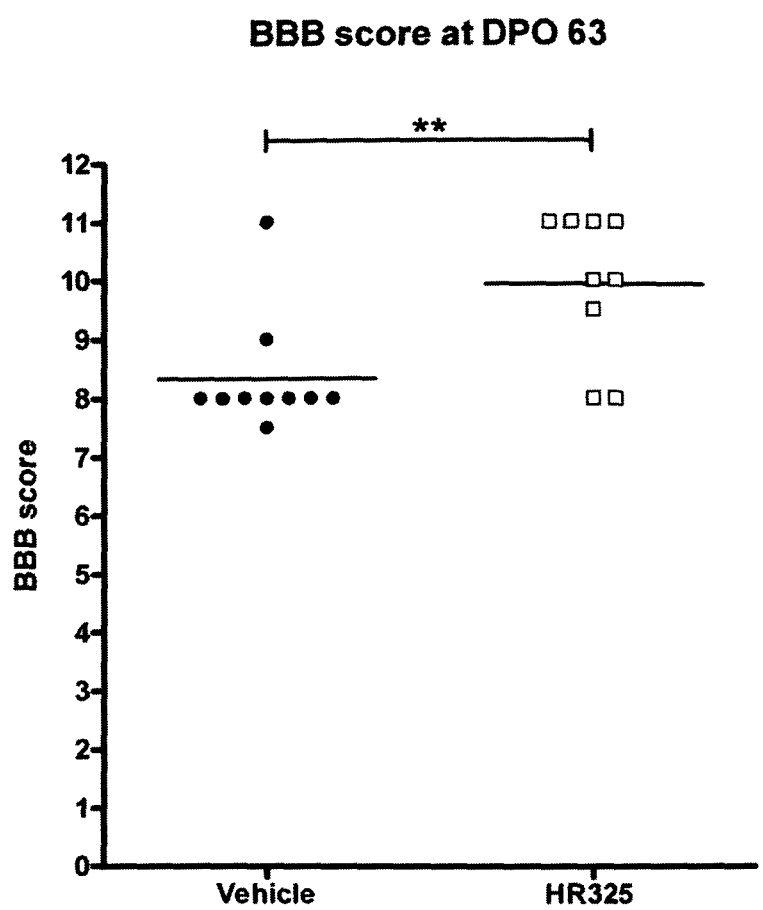

At the end of the experiment the HR325 treated animals performed significantly better as compared to the vehicle controls (Mann-Whitney U Test; p=0.006, see FIG. 5). FIG. 5 shows individual BBB scores of the HR325 and Vehicle treated animals at DPO 63 (**p<0.01).

The explorative rearing test was used to assess other aspects of functional recovery after injury. One of the parameters that reflect the degree of functional recovery in this test is the time each animal spend in the different rearing heights. The results of this parameter are presented in FIG. 6.

Figure 6:
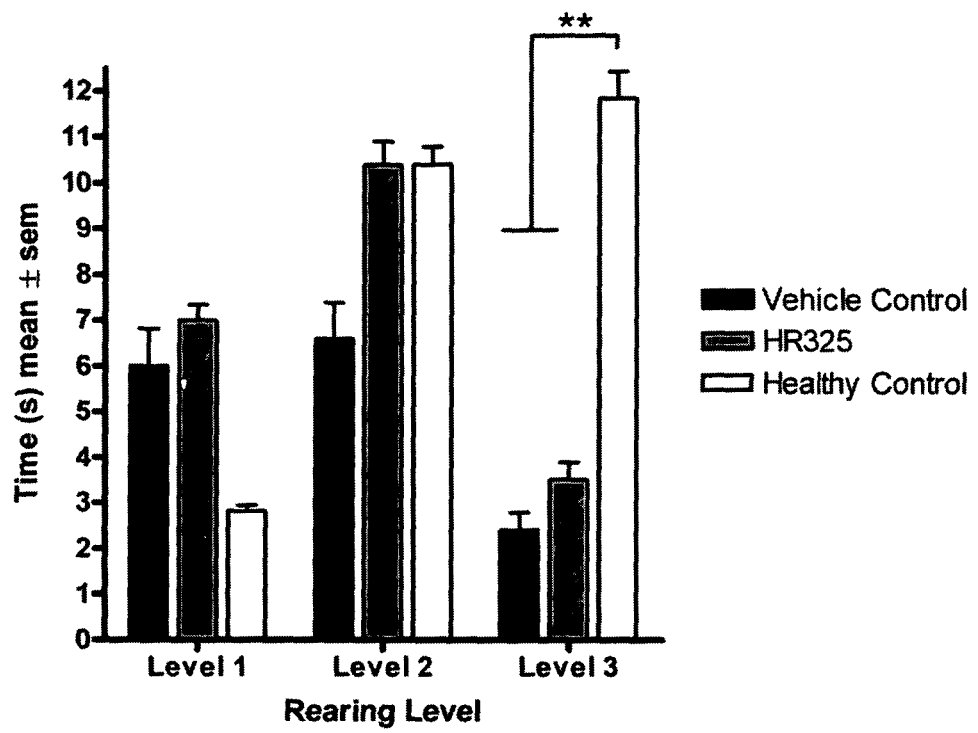

These results clearly demonstrate that the rearing attempts of HR325 treated animals are longer in time and that the forepaws reached higher when compared to vehicle control animals. This effect was noticeable predominantly at LEVEL 2 (see FIG. 6) in which HR325 treated and healthy control animals spend an equal amount of exploring time at this level. At LEVEL 3 (>15 cm) the impairment as a consequence of the spinal cord contusion becomes obvious, the healthy control animals spend most of their exploring time in the highest level, significantly longer as both HR325 treated animals and vehicle controls. FIG. 6 shows the results of the explorative rearing test in vehicle controls and HR325 treated animals (**p<0.01).

Example 3

HR325 (Laflunimus) treatment with different dosages can improve locomotor recovery after severe spinal cord contusion injury in the rat.

For surgical methods see example 1.

After injury, individual rats were randomly assigned into a treatment group. The following groups were used:
Group 1: SCI+vehicle (1.5% CMC in sterile water) by gavage for 7 days
Group 2: SCI+HR325 (3 mg/kg/day) in vehicle by gavage for 7 days
Group 3: SCI+HR325 (20 mg/kg/day) in vehicle by gavage for 7 days
Group 4: SCI+HR325 (60 mg/kg/day) in vehicle by gavage for 7 days For the BBB open field locomotor rating scale see example 1.

For the explorative rearing test see example 1.

Results:

Functional Recovery

Figure 7:
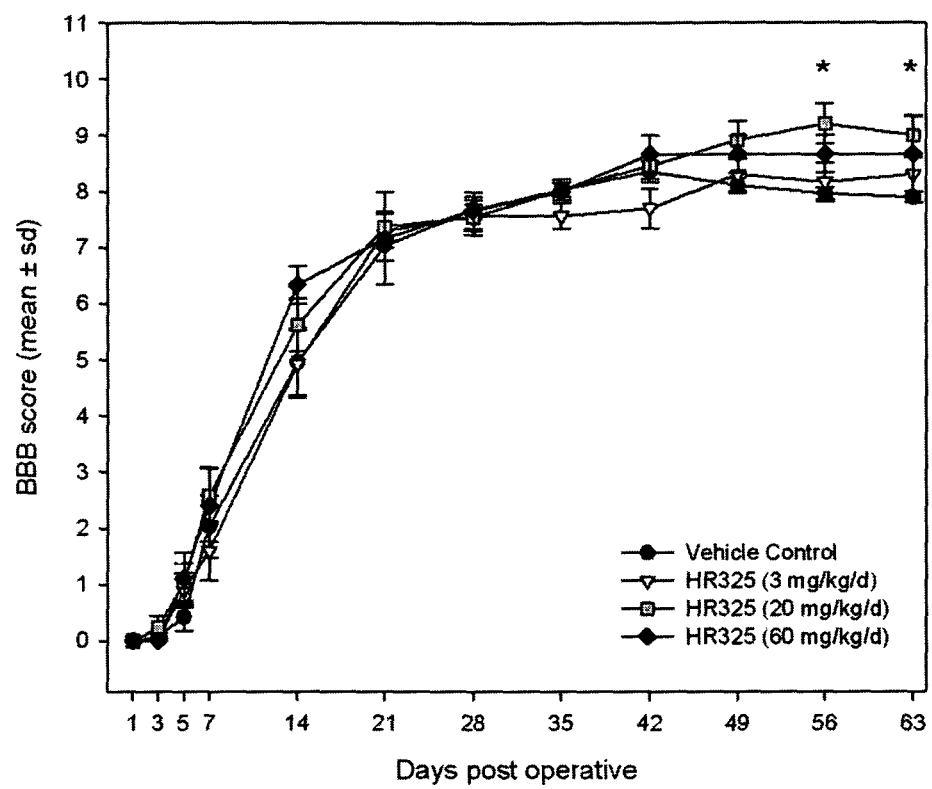
Figure 8:
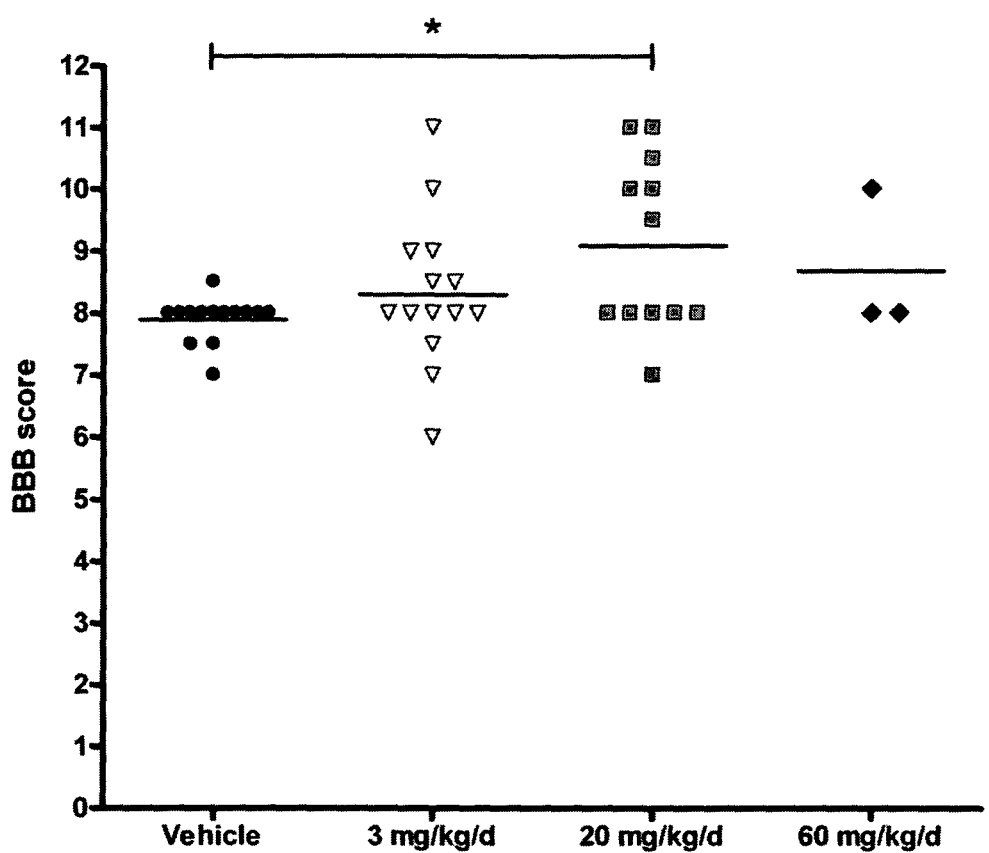

The functional recovery as assessed by the BBB locomotor rating scale followed, as in the previous examples, a pattern of progressive recovery over the first 2-3 weeks after injury. Thereafter the spontaneous functional recovery reached a 'steady state'. Statistically significant differences were noted at DPO 56, the 20 mg HR325 treated animals performed significantly better then vehicle treated animals (one-way ANOVA; Treatment $F_{2,40}$=4.45 p<0.05, see FIG. 7). At the end of the experiment at DPO 63 the significant differences in BBBscore were still observed (one-way ANOVA; Treatment $F_{2,40}$=3.67 p<0.05, see FIGS. 7 and 8, *p<0.05).

Figure 9:
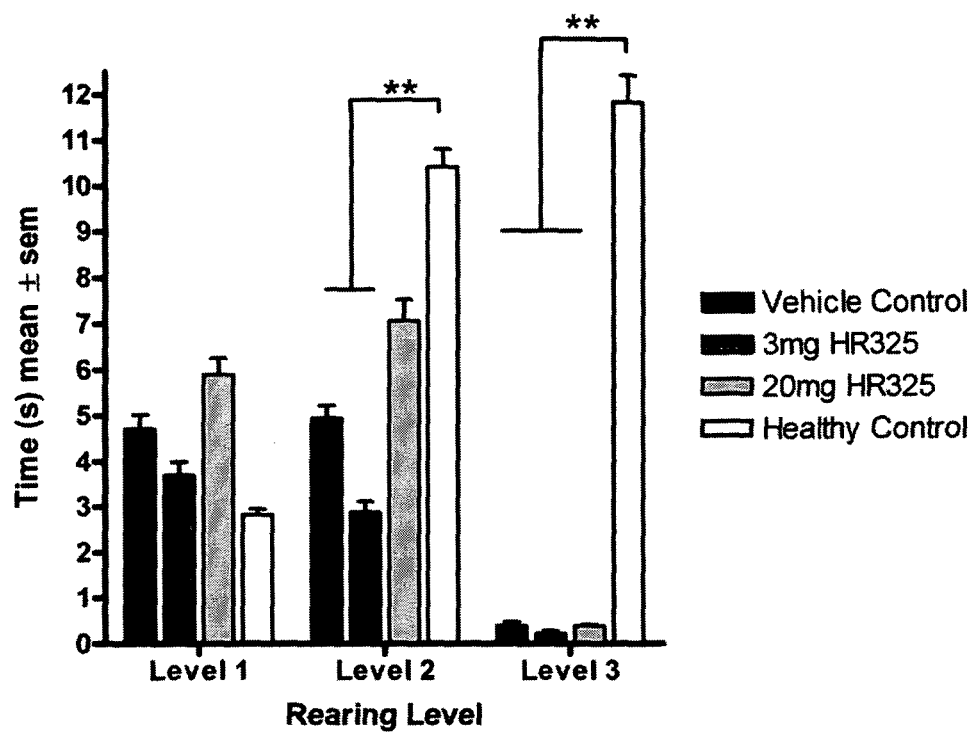

The explorative rearing test was used to assess other aspects of functional recovery after injury. One of the parameters that reflect the degree of functional recovery in this test is the time each animal spend in the different rearing heights. The results of this parameter are presented in FIG. 9.

These results demonstrate that the rearing attempts of 20 mg HR325 treated animals are longer in time and that the forepaws reached much higher when compared to vehicle control animals. All treatment groups showed a comparable exploration time in LEVEL 1. In the physically more demanding rearing level, LEVEL 2 the first differences between the HR325 treatment and vehicle controls became evident. The 20 mg HR325 treated animals performed not significantly different from the healthy controls (**p<0.01).

Example 4

Teriflunomide treatment can improve locomotor recovery after severe spinal cord contusion injury in the rat.

For surgical methods see example 1.

After injury, individual rats were randomly assigned into a treatment group. The following groups were used:
Group 1: SCI+vehicle (1.5% CMC in sterile water) by gavage for 7 days
Group 2: SCI+teriflunomide (3 mg/kg/day) in vehicle by gavage for 7 days
Group 3: SCI+teriflunomide (10 mg/kg/day) in vehicle by gavage for 7 days For the BBB open field locomotor rating scale see example 1.

Results:

Functional Recovery

Figure 10:
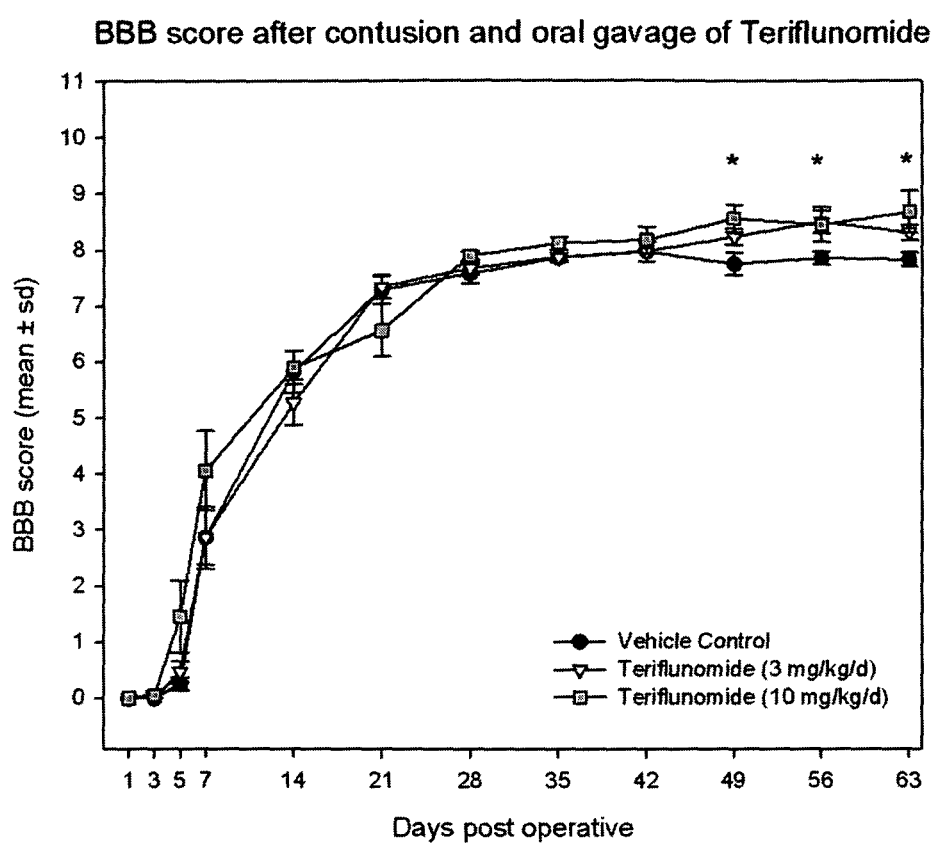
Figure 11:
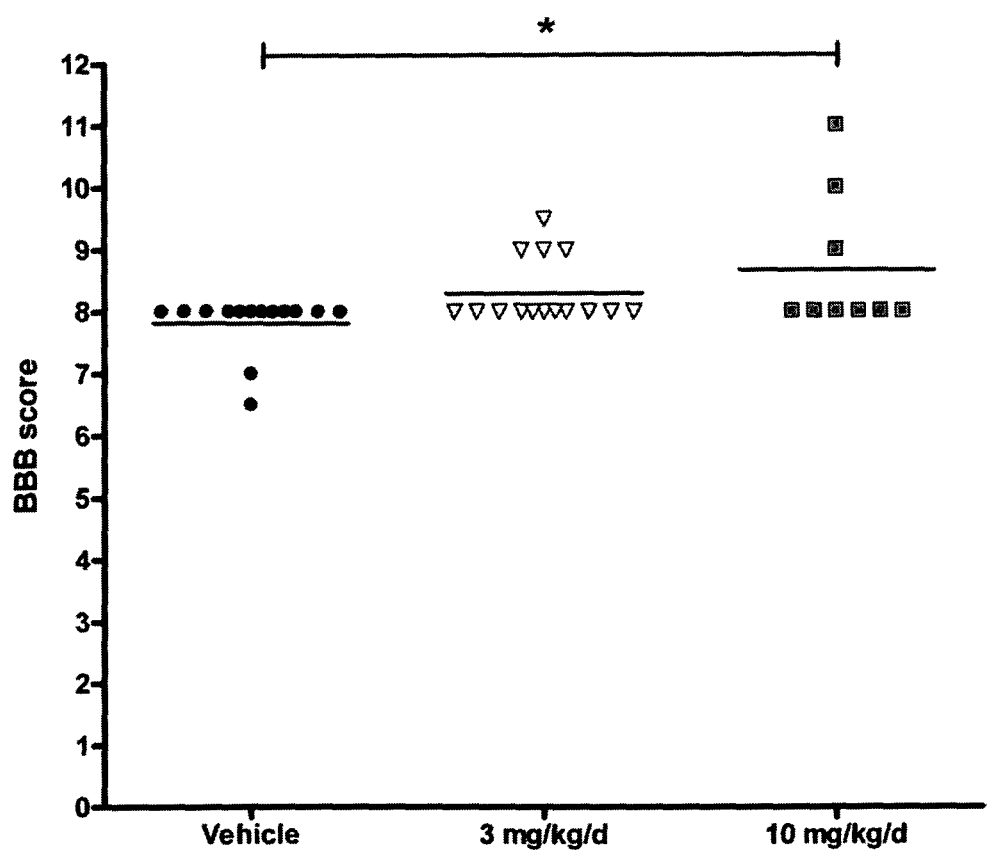

The functional recovery as assessed by the BBB locomotor rating scale followed, as in the previous examples, a pattern of progressive recovery over the first 2-3 weeks after injury. Thereafter the spontaneous functional recovery reached a 'steady state'. Differences between the teriflunomide treated animals and the vehicle control animals emerged relatively late comparable to the previous example. Statistically significant differences were noted at DPO 49, the 10 mg teriflunomide treated animals performed significantly better then vehicle control animals (one-way ANOVA; Treatment $F_{2,37}$=4.30 p<0.05, see FIG. 10). At the end of the experiment at DPO 63 the significant differences in the BBBscore were still observed (one-way ANOVA; Treatment $F_{2,37}$=4.31 p<0.05, see FIGS. 10 and 11). The 3 mg teriflunomide treated animals performed comparable to the vehicle control animals throughout the entire experiment.

Example 5

HR325 (Laflunimus) treatment can improve locomotor recovery after severe spinal cord contusion injury in the rat.

For surgical methods see example 1.

After injury, individual rats were randomly assigned into a treatment group. The following groups were used:
Group 1: SCI+vehicle (1.5% CMC in sterile water) by gavage for 7 days
Group 2: SCI+HR325 (10 mg/kg/day) in vehicle by gavage for 7 days
Group 3: SCI+HR325 (30 mg/kg/day) in vehicle by gavage for 7 days For the BBB open field locomotor rating scale see example 1.

Results:

Functional Recovery

Figure 12:
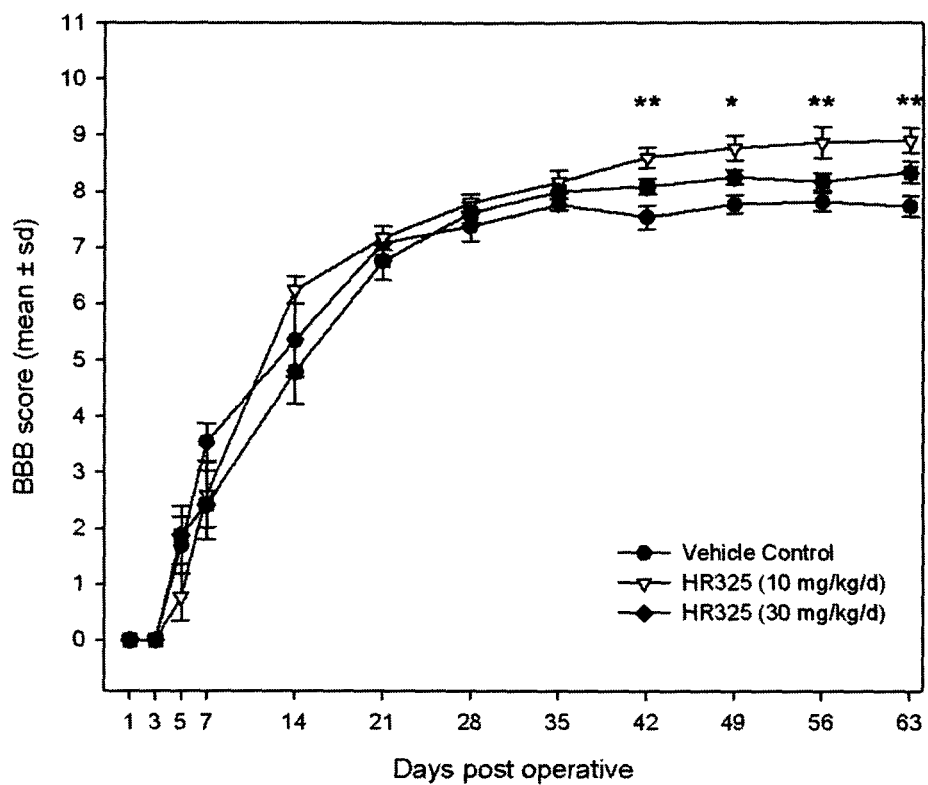
Figure 13:
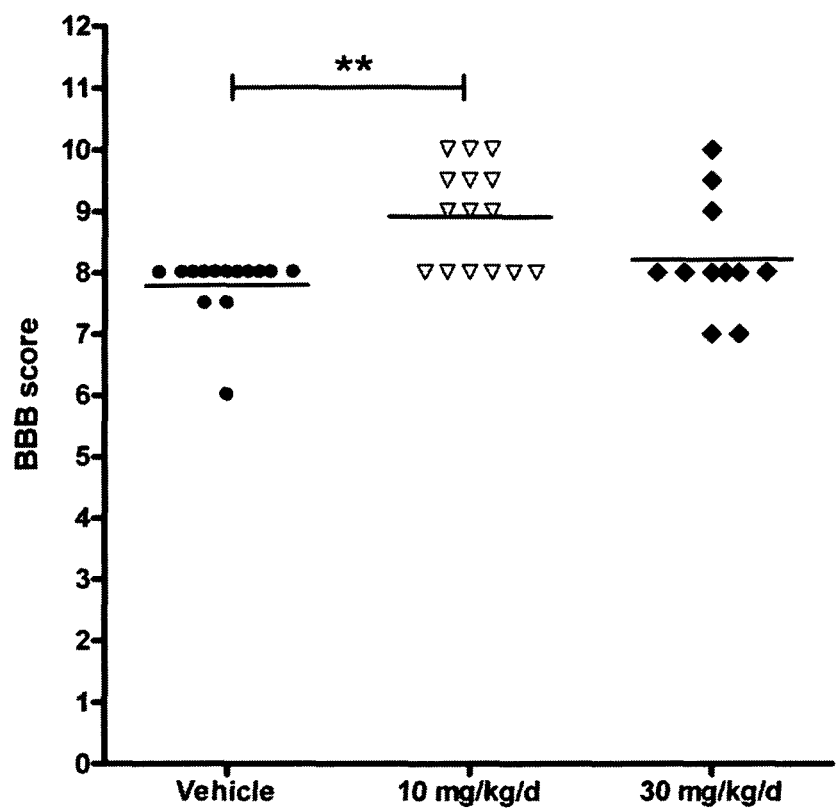

The functional recovery as assessed by the BBB locomotor rating scale followed, as in the previous examples, a pattern of progressive recovery over the first 2-3 weeks after injury. Thereafter the spontaneous functional recovery reached a 'steady state'. Differences between the HR325 treated animals and the vehicle control animals were observed from DPO42 till the end of the experiment. The 10 mg HR325 treated animals performed significantly better at DPO42 then vehicle control animals (one-way ANOVA; Treatment $F_{2,40}$=5.66 p<0.01, see FIG. 12). This difference in BBBscore between the 10 mg HR325 treated animals and the vehicle controls remained till the end of the experiment (one-way ANOVA; Treatment $F_{2,40}$=5.80 p<0.01, see FIGS. 12 and 13).

The 30 mg HR325 treated animals performed comparable to the vehicle control animals throughout the entire experiment.

The results presented in the five examples proof that a controlled pharmacotherapy by compounds according to the present invention like isoxazole-4-carboxamides or malononitrilamides can be used for treating CNS-trauma related disorders like acute spinal cord injury.

The embodiments of the disclosure described above are intended to be merely exemplary, and those skilled in the art will recognize, or will be able to ascertain using no more than routine experimentation, numerous equivalents of specific compounds, materials, and procedures. All such equivalents are considered to be within the scope of the disclosure.

ADDITIONAL REFERENCES

The following additional publications are incorporated herein by references:

Basso, D. M., et al., 1995. A sensitive and reliable locomotor rating scale for open field testing in rats. J. Neurotrauma. 12, 1-21.

Davis, J. P., et al., 1996. The immunosuppressive metabolite of leflunomide is a potent inhibitor of human dihydroorotate dehydrogenase. Biochemistry. 35, 1270-3.

Greene, S., et al., 1995. Inhibition of dihydroorotate dehydrogenase by the immunosuppressive agent leflunomide. Biochem Pharmacol. 50, 861-7.

Himes, B. T., et al., 2006. Recovery of function following grafting of human bone marrow-derived stromal cells into the injured spinal cord. Neurorehabil Neural Repair. 20, 278-96.

Kuo, E. A., et al., 1996. Synthesis, structure-activity relationships, and pharmacokinetic properties of dihydroorotate dehydrogenase inhibitors: 2-cyano-3-cyclopropyl-3-hydroxy-N-[3'-methyl-4'-(trifluoromethyl)phenyl]propenamide and related compounds. J Med Chem. 39, 4608-21.

Shumsky, J. S., et al., 2003. Delayed transplantation of fibroblasts genetically modified to secrete BDNF and NT-3 into a spinal cord injury site is associated with limited recovery of function. Exp Neurol. 184, 114-30.

Williamson, R. A., et al., 1995. Dihydroorotate dehydrogenase is a high affinity binding protein for A77 1726 and mediator of a range of biological effects of the immunomodulatory compound. J Biol Chem. 270, 22467-72.

Zielinski, T., et al., 1995. Leflunomide, a reversible inhibitor of pyrimidine biosynthesis? Inflamm Res. 44 Suppl 2, S207-8.

The invention claimed is:

1. A method for treating a central nervous system-trauma related disorder, which is selected from a spinal cord injury or a spinal cord contusion, comprising administering to a patient in need thereof a therapeutically or prophylactically effective amount of a compound of the formula (III)

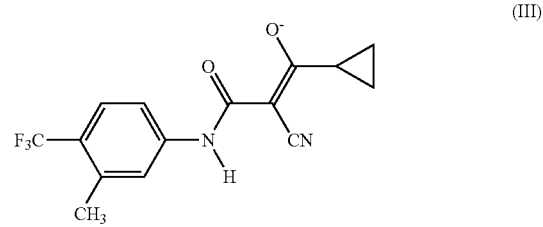 [SMILES: Cc1cc(NC(=O)/C(C#N)=C(\[O-])C2CC2)ccc1C(F)(F)F]

(III)

or a pharmaceutically acceptable salt, solvate, or stereoisomer thereof, optionally in admixture with a pharmaceutical acceptable carrier or excipient.

2. The method of claim 1, wherein the compound is the R or S enantiomer.

* * * * *

UNITED STATES PATENT AND TRADEMARK OFFICE
CERTIFICATE OF CORRECTION

PATENT NO. : 8,957,098 B2
APPLICATION NO. : 13/817800
DATED : February 17, 2015
INVENTOR(S) : Guido Koopmans, Birgit Hasse and Stefan Mullner Page 1 of 1

It is certified that error appears in the above-identified patent and that said Letters Patent is hereby corrected as shown below:

Title Page, (87), replace "PCT Pub. No.: WO2012/028278" with --PCT Pub. No.: WO2012/025217--.
Title Page, (87), replace "PCT Pub. Date: Mar. 8, 2012" with --PCT Pub. Date: Mar. 1, 2012--.

Signed and Sealed this
Twenty-second Day of September, 2015

Michelle K. Lee
*Director of the United States Patent and Trademark Office*